United States Patent
Vibert et al.

(10) Patent No.: US 10,941,100 B2
(45) Date of Patent: Mar. 9, 2021

(54) METHOD FOR THE PURIFICATION OF NATURAL VANILLIN

(71) Applicant: RHODIA OPERATIONS, Paris (FR)

(72) Inventors: Martine Vibert, Lyons (FR); Alain Etchebarne, Melle (FR)

( * ) Notice: Subject to any disclaimer, the term of this patent is extended or adjusted under 35 U.S.C. 154(b) by 0 days.

(21) Appl. No.: 16/484,020

(22) PCT Filed: Feb. 8, 2018

(86) PCT No.: PCT/EP2018/053207
§ 371 (c)(1),
(2) Date: Aug. 6, 2019

(87) PCT Pub. No.: WO2018/146210
PCT Pub. Date: Aug. 16, 2018

(65) Prior Publication Data
US 2019/0389792 A1    Dec. 26, 2019

(30) Foreign Application Priority Data

Feb. 8, 2017 (FR) ...................................... 1751021

(51) Int. Cl.

| | | |
|---|---|---|
| *C07C 45/00* | (2006.01) | |
| *A23L 27/00* | (2016.01) | |
| *C07C 49/258* | (2006.01) | |
| *A23L 27/10* | (2016.01) | |
| *B01D 1/22* | (2006.01) | |
| *B01D 3/00* | (2006.01) | |
| *B01D 3/14* | (2006.01) | |
| *B01D 3/34* | (2006.01) | |
| *B01D 9/00* | (2006.01) | |
| *A23L 27/24* | (2016.01) | |

(52) U.S. Cl.
CPC .......... *C07C 49/258* (2013.01); *A23L 27/115* (2016.08); *B01D 1/22* (2013.01); *B01D 3/002* (2013.01); *B01D 3/148* (2013.01); *B01D 3/346* (2013.01); *B01D 9/0059* (2013.01); *A23L 27/24* (2016.08); *A23V 2002/00* (2013.01); *B01D 2009/0086* (2013.01); *C07B 2200/13* (2013.01)

(58) Field of Classification Search
CPC ............................. C07C 45/258; A23L 27/115
See application file for complete search history.

(56) References Cited

U.S. PATENT DOCUMENTS

| | | |
|---|---|---|
| 2,745,796 A | 5/1956 | Toppel |
| 5,017,388 A | 5/1991 | Rabenhorst et al. |
| 5,658,433 A | 8/1997 | Baird |
| 2014/0316165 A1 | 10/2014 | Vibert et al. |

FOREIGN PATENT DOCUMENTS

| | | |
|---|---|---|
| DE | 1132113 B | 6/1962 |
| EP | 0885968 A1 | 12/1998 |
| GB | 1049427 A | 11/1966 |
| WO | 2014114590 A1 | 7/2014 |
| WO | 2013087795 A1 | 10/2014 |

OTHER PUBLICATIONS

"Preparation of lignin from wood dust as vanillin source and comparison of different extraction methods", International journal of Biology and biotechnology, Jan. 1, 2004 pp. 535-537.

*Primary Examiner* — Sikarl A Witherspoon
(74) *Attorney, Agent, or Firm* — Osha Bergman Watanabe & Burton LLP

(57) ABSTRACT

The present invention relates to a method for the purification of natural vanillin, comprising a step involving the stripping of a liquid flow F2 containing natural vanillin. The invention also relates to the natural vanillin that can be obtained using the method of the invention, as well as a device for purifying natural vanillin.

15 Claims, 1 Drawing Sheet

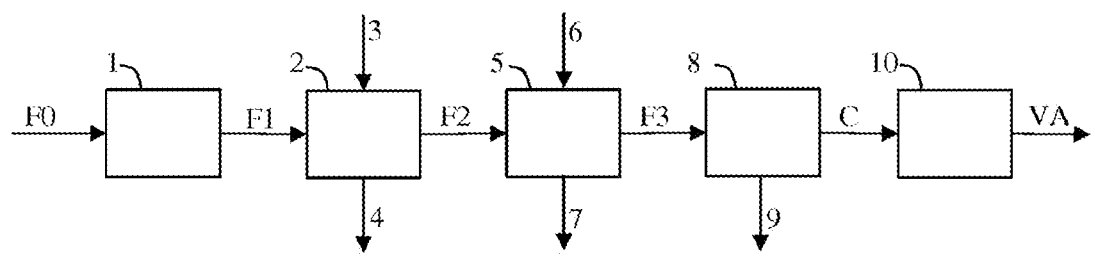

and … "
METHOD FOR THE PURIFICATION OF NATURAL VANILLIN

This application is a U.S. national stage entry under 35 U.S.C. § 371 of International Application No. PCT/EP2018/053207 filed 8 Feb. 2018, which claims priority to FR 1751021 filed on 8 Feb. 2017. The entire content of each of these applications is hereby incorporated herein by reference.

TECHNICAL FIELD

The present invention relates to a process for purifying natural vanillin. The invention also relates to the natural vanillin capable of being obtained by the process according to the invention and also to a device for producing natural vanillin.

PRIOR ART

Vanillin may be obtained by different methods known to a person skilled in the art, in particular by the following two routes:
- A "natural" route based on a biotechnological process comprising in particular the culturing of a microorganism capable of making possible the bioconversion of a fermentation substrate into vanillin. Such a process in which the fermentation substrate is ferulic acid is in particular known from Application EP 0 885 968. U.S. Pat. No. 5,017,388 describes a process in which the fermentation substrate is eugenol and/or isoeugenol. These processes result in the preparation of a vanillin termed natural vanillin.
- A "synthetic" route comprising conventional chemical reactions starting from guaiacol not involving a microorganism. This process results in the preparation of a vanillin termed synthetic vanillin.

Finally, vanillin may also be prepared according to a route described as natural in which vanillin results from lignin; mention may in particular be made of the documents U.S. Pat. No. 2,745,796 and DE1132113 and the paper entitled "Preparation of lignin from wood dust as vanillin source and comparison of different extraction methods" by Azadbakht et al. in International Journal of Biology and Biotechnology, 2004, Vol. 1, No. 4, pp 535-537.

Currently, natural vanillin may be purified according to the process described in Application EP 2 791 098, which comprises a step of liquid/liquid extraction of impurities having a higher pKa than that of vanillin. The yield of this process is good, generally greater than 80%; however, in order to obtain improved qualities with regard to the color of the vanillin, several additional purification steps are necessary, thus bringing about a fall in the overall yield of this process.

International Application WO 2014/114590 also describes a process for the purification of natural vanillin. This process consists in evaporating natural vanillin, it being possible for this evaporation to be carried out by distillation or by vacuum evaporation of molten vanillin. This process is capable of producing very pure natural vanillin, with a good yield, with a device which is simple to employ and which operates continuously in order to be compatible with industrial processes. However, such a process might be difficult to put into practice due to the number and the scale of the items of equipment necessary.

This is why it would be advantageous to have available a simpler process, with respect to those provided in the prior art.

One of the objectives of the present invention is to provide a process having an improved overall yield while obtaining a vanillin exhibiting a markedly improved coloring, in particular a coloring in 10% ethanolic solution of less than or equal to 100 Hazen, preferably of less than or equal to 50 Hazen, more preferably of less than or equal to 20 Hazen and more preferably still of less than or equal to 10 Hazen.

SUMMARY OF THE INVENTION

A first subject matter of the present invention relates to a process for the purification of natural vanillin comprising at least one step (b) of stripping a liquid stream F2 comprising natural vanillin with an entraining gas G1 and/or a vaporized liquid L1.

A second subject matter of the present invention relates to a natural vanillin capable of being obtained according to the process of the present invention, characterized in that it exists in the form of a solid, the color of which, in 10% by weight ethanolic solution, is less than or equal to 400 Hazen, preferably less than or equal to 200 Hazen, more preferably less than or equal to 50 Hazen and more preferably still less than or equal to 20 Hazen.

Finally, a third subject matter of the present invention relates to a device, in particular for the implementation of the process according to the invention, comprising:
- a stripping device,
- a device for removing the impurities which are less volatile than vanillin, preferably in a vacuum film evaporator or in a thin film evaporator.

DETAILED DESCRIPTION OF THE INVENTION

In the context of the present invention and unless otherwise indicated, the expression "between . . . and . . . " includes the limits.

A first subject matter of the present invention relates to a process for the purification of natural vanillin comprising at least one step (b) of stripping a liquid stream F2 comprising natural vanillin with an entraining gas G1 and/or a vaporized liquid L1.

The process according to the invention advantageously makes it possible to obtain natural vanillin with a high titer starting from a liquid stream F2 comprising natural vanillin.

In the present invention, the expression "natural vanillin" may in particular denote a natural flavoring substance according to Article 9.2.c) of the regulation EC 1334/2008, that is to say a flavoring substance obtained by physical, enzymatic or microbiological processes from materials of plant, animal or microbiological origin taken as they are or after conversion thereof for human consumption by one or more of the conventional processes for the preparation of foodstuffs. A natural flavoring substance corresponds to a substance which is naturally present and has been identified in nature. The definitions given by the regulations in force in other countries or regions of the world may also be applied. Moreover, "natural vanillin" may furthermore denote vanillin extracted from vanilla pods.

Advantageously, the liquid stream F2 may result from a process for the production of natural vanillin. In this stream F2, the natural vanillin exists in the form of non-salified vanillin. Preferably, in the liquid stream F2 of natural vanillin, the concentration by weight of vanillin is greater than or equal to 10%, preferably greater than or equal to 30%, more preferably greater than or equal to 50% and more preferably still greater than or equal to 70%, with respect to the total weight of said liquid stream.

Preferably, a process for the production of natural vanillin denotes in this instance a biotechnological process comprising the culturing of a microorganism capable of making possible the bioconversion of a fermentation substrate into vanillin. Very preferably, it is a process for the fermentation of ferulic acid, such as that described in the patent application EP 0 885 968.

Apart from the vanillin, the stream F2 may contain impurities, in particular impurities formed during the production by enzymatic conversion or by fermentation, typically vanillyl alcohol, vanillic acid, dimers and trimers of vanillin (that is to say, compounds exhibiting a backbone having respectively two or three phenyl groups, the dimers advantageously being chosen from diphenylmethanes). When a fermentation of ferulic acid is concerned, the typical impurities may in addition be chosen from ferulic acid, guaiacol and guaiacol derivatives. Finally, the stream F2 may contain traces of stabilizer.

In addition, the stream F2 may comprise a solvent or a mixture of several solvents, such as a food-grade solvent (for example the solvents identified by the FEMA GRAS™ program) or water. However, the concentration by weight of solvent in the liquid stream F2 is preferably less than or equal to 90%, more preferably less than or equal to 70%, more preferably less than or equal to 50% and more preferably still less than or equal to 30%, with respect to the total weight of said liquid stream.

The process according to the invention may be carried out according to a continuous operation or according to a batchwise operation.

The stripping is a step of entraining via an entraining gas or a vaporized liquid. This is because impurities are entrained by the gas or vaporized liquid, so as to improve the quality of the vanillin.

In particular in the context of the present invention, the stripping step makes it possible advantageously to remove certain impurities present in the stream of natural vanillin.

Such a stripping step may be carried out under mild conditions, in particular by injection of a gaseous fluid or of a liquid and/or placing under vacuum the chamber where the process according to the invention is carried out.

In the context of the present invention, the entraining gas G1 or the vaporized liquid L1 is chosen from the group consisting of water, steam, alkyl acetates, alcohols, inert gases chosen from $N_2$, $CO_2$, He, Ar, depleted air and their mixtures. Preferably, the entraining gas G1 or the vaporized liquid L1 is water or steam. The use of a mixture of several entraining gases G1 and/or of several vaporized liquids L1 may be envisaged.

Step (b) may be carried out at a temperature of greater than or equal to 20° C., preferably of greater than or equal to 30° C., more preferably of greater than or equal to 40° C. and more preferable still of greater than or equal to 50° C. Step (b) may be carried out at a temperature of less than or equal to 140° C., preferably of less than or equal to 120° C., more preferably of less than or equal to 100° C. and more preferable still at 95° C. According to one embodiment of the present invention, step (b) is carried out under decreasing vacuum ranging from 400 mbar to 25 mbar.

According to a first embodiment, the stripping step is carried out with an entraining gas G1, preferably with steam. This embodiment may be carried out continuously in a stripping column: typically, the liquid stream F2 is introduced into the stripping column via the top, while the entraining gas G1 is introduced via the bottom. During their contact, the entraining gas becomes charged with impurities present in the liquid stream and is extracted via the top of the column, while the purified liquid stream is recovered at the column bottom.

According to a second embodiment, the stripping step is carried out with a vaporized liquid L1, preferably with water. This embodiment may be implemented continuously or batchwise in a reactor: typically, the liquid stream F2 and the liquid L1 are mixed in the reactor. Then, by reducing the pressure and/or increasing the temperature, the liquid L1 vaporizes. The vaporized liquid L1 is then extracted from the reactor, entraining with it impurities present in the liquid stream. Said liquid stream, thus purified, may then be recovered in the reactor.

Preferably, the stripping step (b) is carried out under an inert atmosphere and more preferably under $N_2$.

According to a preferred embodiment, the process for the purification of natural vanillin according to the invention may additionally comprise a preliminary step (a) of preparation of said liquid stream F2 of natural vanillin by evaporating, optionally in the presence of water, the solvent S1 of a stream F1 originating from the production of natural vanillin.

This is because, during the production of natural vanillin, it is typical to recover a liquid stream comprising natural vanillin, impurities and a large amount of solvent, typically a food-grade solvent, such as, for example, ethyl acetate. This stream is typically denoted "crude vanillin solution". The process according to the invention may comprise a step of making available a liquid stream F1 resulting from a process for the production of natural vanillin comprising natural vanillin in a solvent S1. Mention may be made, among the solvents S1, for example, of the organic solvents authorized by the regulations, such as MEK (methyl ethyl ketone), alcohols (ethanol, butanol, and the like), alkyl acetates (ethyl acetate, propyl acetate, isopropyl acetate, and the like), MIBK (methyl isobutyl ketone) and cyclohexane. The solvent S1 may also be water. The solvent S1 may also be a mixture of organic solvents, in particular a mixture of the organic solvents mentioned above, or a mixture of water and of an organic solvent.

According to one embodiment, the liquid stream F1 may additionally comprise a stabilizer for the fermentation medium. The bacteriostatic agents (or biocides) which may be employed as stabilizers are well known to a person skilled in the art, for example sorbic acid, benzoic acid, acetic acid and their salts. The stabilizer for natural vanillin in the liquid stream F1 is generally present in an amount of less than or equal to 20% by weight, preferably of less than or equal to 10% by weight. The liquid stream F2 may consequently contain traces of said stabilizers. However, the stream F1 may also be devoid of stabilizer, in particular when the stabilization of the fermentation medium has been carried out in another way. For example, the liquid stream F1 may have been stabilized by heat treatment. This heat treatment makes it possible to halt the action of the microorganisms. The temperature of the heat treatment is generally greater than or equal to 35° C. and generally less than or equal to 110° C., preferably between 50° C. and 110° C.

According to a specific embodiment of the present invention, the process additionally comprises a preliminary step, before step (a) or before step (b), of washing the stream resulting from the process for the production of natural vanillin. This washing may be carried out using an aqueous solution, in order to remove the acidic impurities. In general, this washing may be carried out with a basic solution, preferably a sodium hydroxide solution.

Preferably, in the stream F1, the concentration by weight of the vanillin is from 0.5% to 60%, more preferably from 5% to 40% and more preferably still from 10% to 35%, with respect to the total weight of said stream.

The optional step (a) according to the present invention consists in removing the solvent S1 in order to obtain a stream F2 of vanillin in which the concentration by weight of vanillin is greater than or equal to 10%, preferably greater than or equal to 30%, more preferably greater than or equal to 50% and more preferably still greater than or equal to 70%, with respect to the total weight of said stream. The residual content of solvent S1 is preferably less than or equal to 90%, more preferably less than or equal to 70%, more preferably less than or equal to 50% and more preferably still less than or equal to 30%, with respect to the total weight of said liquid stream.

In accordance with the process according to the invention, the evaporation step (a) may optionally be carried out in the presence of water, which is added to the stream F1 before and/or during the implementation of said evaporation step.

In a preferred embodiment, in the context of step (a), the solvent S1 for the crude vanillin is removed by evaporation, for example by distillation or by means of an evaporator, in the presence of water. The water and the solvent S1 may form an azeotropic mixture. In the case of an evaporation by distillation, the solvent S1 may be distilled at atmospheric pressure or under vacuum or alternatively at atmospheric pressure and then under vacuum. The water may be added in one or more goes to the stream F1. It is preferable to use food-grade water (for example municipal water). It is also possible to use recycled food-grade water originating from the process according to the present invention.

Preferably, said evaporation step (a) is carried out at a temperature of between 60° C. and 140° C. and very preferably between 80° C. and 100° C.

After step (b), the process for the purification of natural vanillin according to the invention may additionally comprise a step (c) of removal of the less volatile compounds than vanillin. This step may advantageously be carried out in a vacuum film evaporator or in a thin film evaporator.

The temperature of the heat-exchange fluid at which step (c) is carried out is generally greater than or equal to 130° C., preferably greater than or equal to 145° C., and less than or equal to 230° C., preferably less than or equal to 180° C. The pressure at which step (c) is carried out is generally greater than or equal to 0.4 mbar, preferably greater than or equal to 1 mbar, and generally less than or equal to 75 mbar, preferably less than 8 mbar and more preferably less than or equal to 4 mbar.

This evaporation step (c) may be facilitated by the use of technical adjuvants, for example by the addition of a fluidifier. Thus, according to a specific embodiment of the present invention, a fluidifier agent authorized by regulations on foodstuffs, for example polyethylene glycol, may be added to natural vanillin between step (b) and step (c), or during step (c).

On conclusion of said step (c), a natural vanillin condensate which is not colored is advantageously obtained. Said natural vanillin condensate preferably has a color of less than or equal to 400 Hazen, preferably of less than or equal to 200 Hazen, more preferably of less than or equal to 100 Hazen, more preferably of less than or equal to 50 Hazen and more preferably still of less than or equal to 20 Hazen (in 10% by weight ethanolic solution).

The process according to the present invention may additionally comprise a step (d) of forming natural vanillin, preferably by crystallization, more preferably by crystallization from a solvent identified by the FEMA GRAS™ program. In a preferred embodiment, the natural vanillin is crystallized or recrystallized from water or from an alcohol/water mixture. The vanillin thus obtained is in the form of white crystals. According to a preferred embodiment of the invention, the solvent used is compatible with regulations making possible the manufacture of products which may be used in the food industry.

The natural vanillin capable of being obtained according to the process of the invention is characterized in that it exists in the form of a solid, the color of which, in 10% by weight ethanolic solution, is less than or equal to 200 Hazen, preferably less than or equal to 100 Hazen, preferentially less than or equal to 50 Hazen, more preferentially less than or equal to 20 Hazen (in 10% by weight ethanolic solution).

Its titer of vanillin is advantageously greater than or equal to 95%, preferably greater than or equal to 99%, more preferably greater than or equal to 99.5%.

The natural vanillin capable of being obtained according to the process of the invention is characterized in that it exhibits a conforming organoleptic profile.

The natural vanillin capable of being obtained according to the process of the invention exhibits specific impurities. The impurities present in the natural vanillin obtained according to the process of the invention are linked to the process for the preparation of said natural vanillin. Thus, the impurities present in a natural vanillin fermentation must resulting from ferulic acid are different from those obtained in a eugenol or isoeugenol fermentation must. Furthermore, the purification methods make it possible to remove certain impurities and in variable amounts; thus, on conclusion of the purification step, the natural vanillin will exhibit impurities which are specific to its process of preparation and specific to its process of purification.

The inventors have discovered that, entirely surprisingly, the natural vanillin resulting from a fermentation process and purified in accordance with the invention exhibits a conforming organoleptic profile, in particular in terms of visual appearance, of texture, of taste and of smell.

Compared with the processes of the prior art, the purification process according to the present invention makes it possible to purify the natural vanillin with a yield of greater than or equal to 70%, preferably of greater than or equal to 80%, more preferably of greater than or equal to 90%. The natural vanillin obtained advantageously exhibits a very high titer of vanillin, it is white in color and exhibits a conforming organoleptic profile, without false notes, as shown in the examples. The evaluation of the conformity may in particular be carried out by a trained panel in a triangle test with respect to the reference. The standard ISO 4120:2004(f) defines the minimum number of correct responses for establishing a significant difference.

The present invention also relates to a device, in particular for the implementation of the process, comprising:
 a stripping device,
 a device for removing the impurities which are less volatile than vanillin, preferably a vacuum film evaporator or a thin film evaporator.

Said device may optionally comprise, in addition:
 a washing device, capable of washing a crude vanillin solution, and/or
 a distillation device, capable of evaporating the solvent from the crude vanillin solution, and/or means for forming the purified natural vanillin, preferably crystallization means.

A specific but nonlimiting embodiment of the process according to the invention is represented in FIG. 1.

According to this embodiment, a solution of crude vanillin (F0) is obtained by a process for the production of natural vanillin. The solution comprises natural vanillin in a solvent S1 and impurities typical of the production process. This solution F0 is washed using a sodium hydroxide solution in a washing device (1). The stream (F1) obtained comprises natural vanillin in the solvent S1 and a reduced content of acidic impurities.

The stream (F1) is introduced into a distillation device (2), so as to evaporate the solvent S1. Water is optionally introduced in (3). While the solvent S1 and the water are discharged in (4), a stream (F2) advantageously comprising more than 70% of natural vanillin is recovered.

The stream (F2) is introduced into a stripping device (5). The impurities are removed by an entraining gas G1 and/or a vaporized liquid L1 introduced in (6) and discharged in (7).

The purified stream of natural vanillin (F3) is then treated in a vacuum film evaporator or a thin film evaporator (8). The heavy compounds are separated in (9) and a natural vanillin condensate (C) of high purity and which is colorless is obtained.

Said condensate (C) may be crystallized in (10), in order to obtain the natural vanillin (VA) in the form of white crystals.

The present invention will now be illustrated by examples which do not exhibit a nature which limits the invention.

EXAMPLES

Example 1

The process illustrated in FIG. 1 was carried out starting from a stream resulting from a process for the production of natural vanillin in solution. This stream exhibited the following composition:

| Compound | Percentage by weight |
| --- | --- |
| Vanillin | 17.3% |
| Vanillyl alcohol | 2.3% |
| Benzoic acid | 1.5% |
| Guaiacol | 0.1% |

This stream was subjected to a first step of washing with an aqueous sodium hydroxide solution. The stream obtained on conclusion of this step comprises the following compounds:

| Compound | Percentage by weight |
| --- | --- |
| Vanillin | 16.9% |
| Vanillyl alcohol | 1.9% |
| Benzoic acid | 0.3% |
| Guaiacol | 0.1% |

A step (a) of distillation in the presence of water was carried out at a temperature of 80° C. under a pressure of 100 mbar. The stream at the outlet comprised the following compounds:

| Compound | Percentage by weight |
| --- | --- |
| Vanillin | 78.1% |
| Vanillyl alcohol | 10.0% |
| Benzoic acid | 1.5% |

A step (b) of stripping was carried out on the stream obtained on conclusion of step (a), at a temperature of 90° C., using, as entraining liquid, water which is vaporized under the operating conditions: liquid water was added at atmospheric pressure and then the pressure was lowered down to 25 mbar. The stream at the outlet comprised the following compounds:

| Compound | Percentage by weight |
| --- | --- |
| Vanillin | 74.5% |
| Vanillyl alcohol | 8.5% |
| Benzoic acid | 1.2% |

A step (c) in a thin film evaporator was subsequently carried out. The stream at the outlet comprised the following compounds:

| Compound | Percentage by weight |
| --- | --- |
| Vanillin | 92.4% |
| Vanillyl alcohol | 6.6% |

Finally, a step (d) of crystallization was carried out on the product obtained at the outlet of step (c). The vanillin obtained on conclusion of this purification process exhibits a titer of 99.6% and is obtained with a yield of 87%.

The vanillin thus purified exhibits a colorimetry of 18 Hazen.

A sensory analysis according to a triangle test was carried out in conformity with the standard ISO 4120/2004 relating to triangle tests. The sensory analysis is carried out on a panel made up of 7 to 11 people. After carrying out this sensory analysis, it was concluded that the organoleptic qualities of the vanillin obtained are in accordance with the reference, the reference in this instance being the Rhovanil® Natural CW commercial vanillin.

Example 2

The procedure as in example 1 is carried out, except that the initial stream exhibited the following composition:

| Compound | Percentage by weight |
| --- | --- |
| Vanillin | 20.3% |
| Vanillyl alcohol | 2.3% |
| Benzoic acid | 0% |
| Guaiacol | 0.3% |
| Other impurities | 0.7% |

The washing step was not carried out. After distillation, the stream at the outlet comprised the following compounds:

| Compound | Percentage by weight |
| --- | --- |
| Vanillin | 85.6% |
| Vanillyl alcohol | 9.7% |

-continued

| Compound | Percentage by weight |
| --- | --- |
| Guaiacol | 1.3% |
| Other impurities | 3.4% |

The stripping was carried out with steam. For this, 600 g of the stream to be treated were placed in a 1-liter reactor provided with a condenser. Low-pressure steam was injected by a dip pipe at 104-108° C. for 3 h. The stream at the outlet comprised the following compounds:

| Compound | Percentage by weight |
| --- | --- |
| Vanillin | 96.6% |
| Vanillyl alcohol | 9.5% |
| Other impurities | 3.9% |

After passing through a thin film evaporator, the stream at the outlet comprised the following compounds:

| Compound | Percentage by weight |
| --- | --- |
| Vanillin | 90.2% |
| Vanillyl alcohol | 9.2% |

After crystallization, the vanillin exhibited a titer of 99.5%.

The invention claimed is:

1. A process for the purification of natural vanillin resulting from a biotechnological process, comprising: stripping a liquid stream comprising natural vanillin with an entraining gas and/or a vaporized liquid, in which the concentration by weight of natural vanillin in the liquid stream is greater than or equal to 10%,
    wherein a 10% by weight ethanolic solution of the natural vanillin obtained in the step of stripping the liquid stream comprising natural vanillin with an entraining gas has a color of less than or equal to 50 Hazen.

2. The process as claimed in claim 1, in which the concentration by weight of natural vanillin in the liquid stream is greater than or equal to 30%.

3. The process as claimed in claim 1, additionally comprising preparing the liquid stream of natural vanillin by evaporating, optionally in the presence of water, a solvent of a stream originating from the production of natural vanillin.

4. The process as claimed in claim 1, further comprising, after the step of stripping the liquid stream comprising natural vanillin with an entraining gas, removing the compounds which are less volatile than vanillin.

5. The process as claimed in claim 1, in which the entraining gas or the vaporized liquid is selected from the group consisting of water, steam, alkyl acetates, alcohols, inert gases selected from $N_2$, $CO_2$, He, Ar, and depleted air, and their mixtures.

6. The process as claimed in claim 1, in which the step of stripping the liquid stream comprising natural vanillin with an entraining gas is carried out at a temperature of greater than or equal to 20° C., and less than or equal to 140° C.

7. The process as claimed in claim 1, in which the step of stripping the liquid stream comprising natural vanillin with an entraining gas is carried out under an inert atmosphere.

8. The process as claimed in claim 1, further comprising forming natural vanillin.

9. A natural vanillin product resulting from a biotechnological process capable of being obtained according to the defined process as claimed in claim 1, wherein the natural vanillin exists in the form of a solid and a 10% by weight ethanolic solution of such natural vanillin has a color of less than or equal to 50 Hazen.

10. The natural vanillin as claimed in claim 9, characterized in that it exhibits a conforming organoleptic profile.

11. The process as claimed in claim 2, in which the concentration by weight of natural vanillin in the liquid stream is greater than or equal to 50%.

12. The process as claimed in claim 4, wherein compounds less volatile than vanillin are removed in a vacuum film evaporator or in a thin film evaporator.

13. The process as claimed in claim 5, in which the entraining gas or the vaporized liquid is water or steam.

14. The process as claimed in claim 6, in which the step of stripping the liquid stream comprising natural vanillin with an entraining gas is carried out at a temperature greater than or equal to 30° C. and less than or equal to 120° C.

15. The process as claimed in claim 8, wherein the step of forming natural vanillin comprises forming natural vanillin by crystallization.

* * * * *